United States Patent [19]
Goldman

[11] 4,040,419
[45] Aug. 9, 1977

[54] SHIELDING HOLDER FOR A SYRINGE HAVING INDIRECT VIEWING MEANS

[76] Inventor: Abraham Goldman, 105-54 Avenue K, Brooklyn, New York, N.Y. 11236

[21] Appl. No.: 654,191

[22] Filed: Feb. 2, 1976

[51] Int. Cl.² .......................... G21F 5/00; A61N 5/00
[52] U.S. Cl. .................................... 128/215; 128/1.1; 128/2 A; 206/365; 250/496; 250/506
[58] Field of Search .................. 176/DIG. 2; 250/515-520, 506, 496-498; 128/1.1, 1.2, 2 A, 215; 220/82 A; 206/364-366

[56] References Cited
U.S. PATENT DOCUMENTS

| 831,103 | 9/1906 | Ripperger | 250/496 X |
| 2,594,970 | 4/1952 | Monk | 250/506 |
| 3,655,985 | 4/1972 | Brown et al. | 250/506 |
| 3,673,411 | 6/1972 | Glasser | 250/506 |
| 3,688,121 | 8/1972 | Ott | 250/520 |

FOREIGN PATENT DOCUMENTS 1,240,121  5/1967  Germany ............................ 250/515

OTHER PUBLICATIONS

Ter-Pogossian, et al.; "Handling of Radioactive Gold for Therapeutic Purposes"; Nucleonics, vol. 10, No. 3, Mar., 1952.

Primary Examiner—Clifford D. Crowder

[57] ABSTRACT

A shielding holder for a syringe made of a dense material of varying thickness to shield the fingers of a user of a syringe within the holder from radiation during use yet permitting the user to see the fluid remaining within the syringe by reflection in a mirror on the holder of the syringe.

4 Claims, 4 Drawing Figures

SHIELDING HOLDER FOR A SYRINGE HAVING INDIRECT VIEWING MEANS

OBJECTS OF THE INVENTION

This invention relates to a holder for syringes which shields the person using the syringe from radiation, especially the fingers of the user holding the syringe holder and syringe during injection of the fluid within the syringe.

An object of the invention is the use of mirror reflectors on the syringe holder, one of which has a lead or dense material protector strip or wedge behind the mirror reflector so that the person injecting the fluid from the syringe can see the fluid remaining in the syringe by reflection in the mirror. The wedge also acts as a stop for the finger tips of the user and facilitates handling during injection of the fluid within the syringe.

Another object is the replacement of high density lead glass used in present syringe holders with viewing mirrors that permit indirect viewing by the person injecting the fluid from the syringe.

Still another object is to reduce the cost of the syringe holder by eliminating the expensive fragile and easily damaged high density lead glass heretofore used with reflecting mirrors preferably made of highly polished non-breakable metal strips.

Another object is that the person using the syringe holder of the invention sees the image of the fluid within the syringe and the graduation numbers on the syringe cylinder in its true actual size position and the position of the plunger and not in a reversed position or of reduced size.

A further object of the invention is the use of a lip or extension at the upper part of the syringe holder to prevent direct exposure to radiation since radiation activity is reflected downwardly and back to the inside of the holder.

Another object is to provide holders for syringes which may be easily and rapidly assembled or disassembled for use and cleaning purposes.

Yet a still further object is to provide such syringe holders with means for fixedly securing the syringe within the holder.

Another object is to provide a shield for a syringe of high density material to provide a maximum shielding against radiation but having a minimum thickness; however, the upper part or top of the syringe holder that carries a mirror may be considerably thinner because of the space between the syringe and the mirror.

Another object is the provision of a light for the holder so that a user may readily view the graduations of the syringe reflected in the mirrors of the holder where insufficient light is not available.

Still another object of the invention is the provision of a syringe and holder therefor which is relatively inexpensive, economical, to manufacture, easy to use and durable, in addition to the other objects heretofore mentioned.

BACKGROUND

Heretofore, syringe holders for shielding radiation have been known, such as shown and described in U.S. Pat. No. 3,596,659 which are made of high-density lead glass material which is fragile, easily damaged, relatively expensive, difficult to cut and has a tendency to shatter during the cutting operating and if dropped.

It is, therefore, important to avoid the objections stated above in order to provide a less expensive shielding holder for a syringe which is easier to handle and which comprises a high density material providing a maximum of shielding with a minimum of thickness.

IN THE DRAWING

Figure 3:
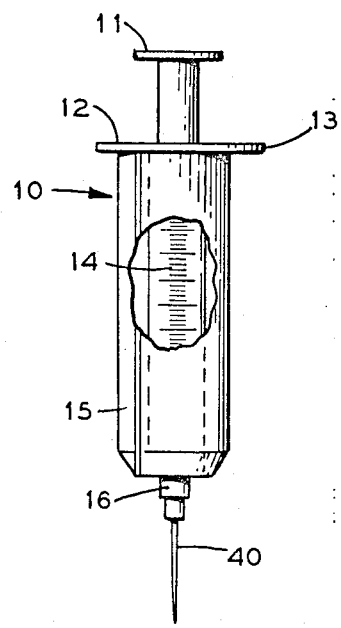
FIG. 3 is a front view of a syringe with a part broken away to show the graduations on the syringe.
Figure 4:
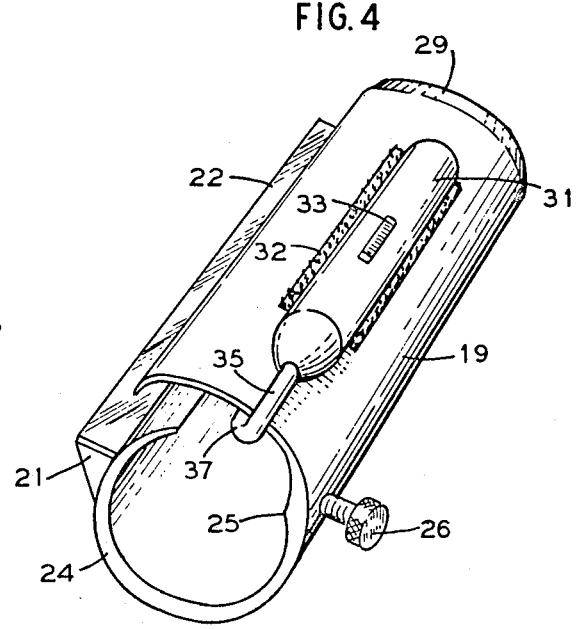
FIG. 4 is a perspective view of a modified holder for a syringe showing a removable flashlight attached to the outside surface with a fiber optic light pipe bent inwardly for lighting the inner part of the holder.

Referring to the drawing, numeral 10 designates a syringe generally known in the medical profession with a hypodermic needle 40 removably attached to one end thereof and a plunger 11 for slidable engagement with the inner surfaces of the cylindrical body of the syringe for injecting a fluid into the body of a person. The forward end portion 15 of the syringe 10 is also provided with an annular boss 16 extending outwardly and provided with means for attaching the hypodermic needle, catheter, or the like and the opposite or handle portion 12 may extend substantially entirely outwardly of the upper end of the cylindrical body portion, as shown in FIG. 3 and may be of generally elongated configuration comprising a pair of opposed ear or flange portions 13. The medial portion of the cylindrical body of the syringe is generally provided with a longitudinal extending scale 14 for indicating the volume contained between the individual markings thereof and the forward end portion 15 or the volume contained within the cylindrical body between the piston of the syringe and the forward end portion 15 when a predetermined portion of the piston is aligned with a particular scale graduation. The scale 14 may be constructed in accordance with conventional practice. The type of syringe is described and pictured in U.S. Pat. No. 3,596,659.

Figure 1:
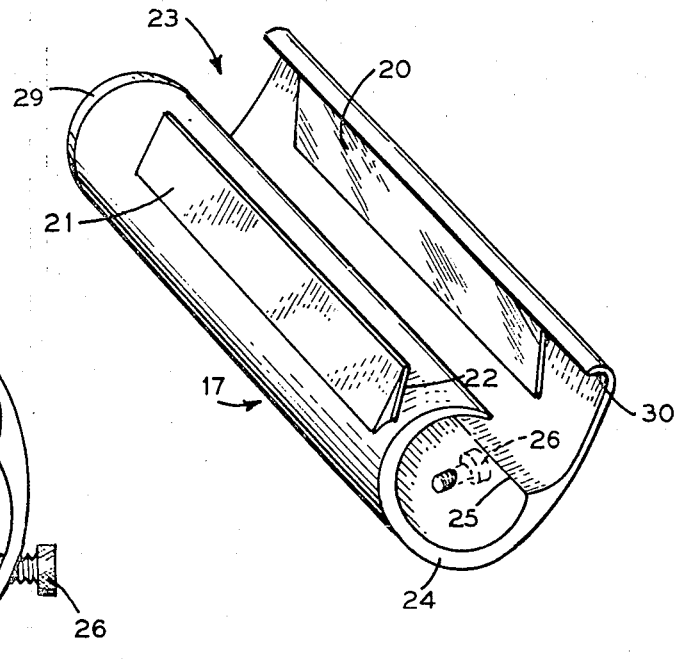
FIG. 1 is a perspective view of the shielding holder for a syringe made in accordance with the principles of the present invention.
Figure 2:
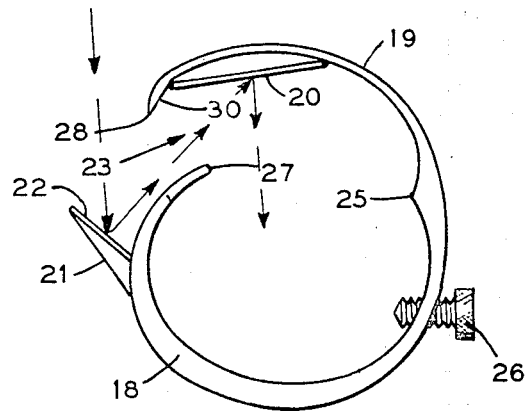
FIG. 2 is an end elevational view of the holder of FIG. 1.

The holder 17 for the syringe 10 is shown in FIGS. 1 and 2 and consists of a dense material, such as lead, depleted uranium, tungsten, or the like and is formed in an arcuate configuration, as best shown in FIGS. 1 and 2, and is of a circumference large enough to circumscribe the cylindrical syringe 10 and long enough to take in the length of the syringe. The holder may be made of different sizes to accommodate different size syringes. The thickness of syringe holder 17 varies in that the lower or bottom portion 18 of the holder has a maximum thickness while it gradually becomes thinner towards the upper portion 19 whereby the bottom or lower portion 18 provides a maximum of shielding against radiation.

At the inner upper longitudinal portion 19 a first mirror 20, preferably made of a highly polished thin metal strip, is attached by any known means, such as by glueing. Along the outer surface of the bottom portion 18, a wedge 21 made of lead or other dense material, such as tungsten, depleted uranium, or the like, is attached by its short side at an appropriate angle longitudinally along the outer surface of said shield or holder 17 for viewing the reflection in a second mirror 22, such reflection coming from mirrow 20.

Second mirror 22 is attached to the inside face of wedge 21, such as by glueing, and is also preferably made of a highly polished thin metal strip.

It should be noted that the holder 17 does not fully enclose the syringe since there is a longitudinal opening 23 between the external edges 27 and 28 of holder 17.

In use the doctor or nurse places the syringe 10 within the holder 17 so that flange 13 of the syringe stops against the upper edge 24 of the holder. The cylindrical syringe 10 lies within the bottom portion 18 and a longitudinal ridge 25 on the inside of the holder. A screw 26 may be turned by the finger of the user to hold the syringe in place within the holder to prevent movement of the syringe within the holder during operation of the plunger 11.

The forward end of the syringe holder is tapered, as shown at 29, to permit ease in vena puncture.

The user then places his fingers around the holder so that the tips of his fingers, or thumb, are behind the outer surface of wedge 21 which acts as protection against reflective radiation and also acts as a supportive stop or surface for the fingers of the user. With his other hand, the user then operates the plunger 11 of the syringe in a standard manner well known in the medical profession.

The lower leading edge 27 of holder 17 extends far enough around the syringe to prevent direct exposure to radiation either horizontally or vertically and extends far enough in relation to leading edge 28 to prevent radiation from directly passing through opening 23.

The user can readily view the quantity of fluid within the syringe as it is being discharged from the syringe at any desired time by viewing or visually observing the discharge by looking at mirror 22 which carries the reflection of the discharge from mirror 20. While viewing is indirect, the dual mirror image is not reversed nor enlarged or reduced in size but reflects the exact size of the graduations on the scale 14.

The dense metal wedge 21 along the longitudinal outer surface of the holder against which the fingers of the user are placed prevents exposure of the fingers to radiation reflecting from the internal surfaces of the syringe shield.

At the upper portion 19 of holder 17 there is a lip 30 which prevents direct exposure to radiation since radiation activity bounces back and is reflected downwardly or inwardly within the holder 17.

Where sufficient light is not available, a means of illumination is provided so that a user of the shielding holder 17 may readily see the graduations of the syringe 10 and the fluid remaining in the syringe. A small battery operated flashlight 31 is removably attached to a magnet 32, or other known means of attachment, such as Velcro, which is preferably attached to the outer surface of the upper portion 19 of the holder by glueing or other known means. The flashlight 31 has an on-off switch 33 which lights a small electric bulb (not shown) which carries the light through a thin fiber optic pipe or rod 35 which passes through an opening of the flashlight. The extreme end 37 of pipe 35 is curved backwardly and lies within one end, preferably the upper end, of the holder and is retained against the inside surface of the holder by a small metal or plastic clamp (not shown) to provide additional light for the user. Of course, a small fiber optic pipe is preferred; however, a very small electric bulb may be substituted for the optic pipe 35. If the user uses the syringe holder during time when the additional light is not necessary, he can readily detach the flashlight 31.

While the invention has been described, illustrated and shown in terms of an embodiment of the invention, the scope of the invention should not be deemed to be limited by the exact embodiment shown, described and illustrated herein.

I claim:

1. A shielding holder for a syringe comprising a holder of high density material, said holder including an open ended arcuate lower portion adapted to receive a syringe therein and having a free lower leading edge, an upper portion integral with said free lower leading edge, said upper portion generally following the arcuate curvature of the arcuate lower portion and overlying the syringe receiving lower portion in upwardly spaced relation thereto, said upper portion extending past and terminating beyond said lower leading edge in an upper leading edge oriented generally parallel to said lower leading edge and in upwardly spaced relation thereto, said leading edges defining an opening therebetween, the orientation of said leading edges relative to each other precluding a direct passage of radiation from a lower portion received syringe through the edge defined opening, and mirror means for viewing a lower portion received syringe through the opening from the exterior of said holder, said mirror means comprising a first mirror positioned within said upper portion generally above said opening for a viewing thereof through said opening, said first mirror facing toward the lower portion, a second mirror and means mounting said second mirror on the exterior of said lower portion below said opening with said second mirror facing said first mirror through said opening for an indirect viewing of a lower portion received syringe by a user looking in said second mirror.

2. The holder defined in claim 1, wherein said means mounting said second mirror comprises an outwardly projecting wedge of dense material mounted on the exterior of said lower portion immediately below said second mirror, said second mirror being attached to said wedge, said wedge acting as a stop for the fingers of a user facilitating handling of said syringe and holder during injection of the material in the syringe and preventing the fingers from exposure to radiation.

3. The holder defined in claim 1, wherein said holder is of varying thickness, said lower portion being thicker than said upper portion.

4. The holder defined in claim 3, wherein said lower portion has an interior longitudinal ridge generally opposed from said leading lower edge for resting against said syringe when said syringe is placed within said lower portion.

* * * * *